United States Patent
Namer Yelin et al.

(10) Patent No.: US 9,875,339 B2
(45) Date of Patent: Jan. 23, 2018

(54) SYSTEM AND METHOD FOR GENERATING A PATIENT-SPECIFIC DIGITAL IMAGE-BASED MODEL OF AN ANATOMICAL STRUCTURE

(75) Inventors: Einav Namer Yelin, Binyaminn (IL); Ran Bronstein, Modiin (IL); Boaz Dov Tal, Airport City (IL)

(73) Assignee: SIMBIONIX LTD., Airport City (IL)

(*) Notice: Subject to any disclaimer, the term of this patent is extended or adjusted under 35 U.S.C. 154(b) by 109 days.

(21) Appl. No.: 13/015,343

(22) Filed: Jan. 27, 2011

(65) Prior Publication Data

US 2012/0197619 A1    Aug. 2, 2012

(51) Int. Cl.
G06G 7/48 (2006.01)
G06F 19/00 (2011.01)
A61B 34/10 (2016.01)

(52) U.S. Cl.
CPC .... *G06F 19/3437* (2013.01); *A61B 2034/105* (2016.02)

(58) Field of Classification Search
None
See application file for complete search history.

(56) References Cited

U.S. PATENT DOCUMENTS

| | | |
|---|---|---|
| 5,371,778 A | 12/1994 | Yanof et al. |
| 6,047,080 A | 4/2000 | Chen et al. |
| 6,062,866 A | 5/2000 | Prom |
| 6,538,634 B1 | 3/2003 | Chui et al. |
| 7,681,579 B2 | 3/2010 | Schwartz |
| 2002/0107573 A1 | 8/2002 | Steinberg |
| 2002/0168618 A1 | 11/2002 | Anderson et al. |
| 2003/0032876 A1* | 2/2003 | Chen et al. .......... 600/407 |
| 2003/0069719 A1 | 4/2003 | Cunningham et al. |
| 2004/0009459 A1 | 1/2004 | Anderson et al. |
| 2004/0015070 A1 | 1/2004 | Liang et al. |
| 2004/0086175 A1 | 5/2004 | Parker et al. |
| 2004/0234933 A1 | 11/2004 | Dawson et al. |
| 2005/0196740 A1 | 9/2005 | Moriyama |
| 2006/0149217 A1 | 7/2006 | Hartlep et al. |
| 2006/0173338 A1 | 8/2006 | Ma et al. |
| 2006/0290695 A1 | 12/2006 | Salomie |
| 2007/0027733 A1 | 2/2007 | Bolle et al. |
| 2007/0043285 A1 | 2/2007 | Schwartz |
| 2007/0049817 A1 | 3/2007 | Preiss et al. |
| 2007/0148625 A1* | 6/2007 | Biltz et al. .......... 434/262 |
| 2007/0231779 A1 | 10/2007 | Santhanam et al. |
| 2009/0006131 A1 | 1/2009 | Unger et al. |
| 2009/0304582 A1 | 12/2009 | Rousso et al. |
| 2009/0310847 A1 | 12/2009 | Matsuzaki et al. |
| 2010/0070249 A1 | 3/2010 | Ionasec et al. |
| 2010/0268068 A1 | 10/2010 | Vass et al. |
| 2011/0092804 A1* | 4/2011 | Schoenefeld et al. .......... 600/416 |

FOREIGN PATENT DOCUMENTS

| | | |
|---|---|---|
| EP | 1418523 | 5/2004 |
| JP | 2004065815 | 3/2004 |
| JP | 2008173159 | 7/2008 |
| WO | WO 2004/051604 | 6/2004 |

OTHER PUBLICATIONS

Wierzbicki et al. Four-Dimensional Modeling of the Heart for Image Guidance of Minimally Invasive Cardiac Surgeries. Medical Imaging 2004: Visualization, Image-Guided Procedures, and Display. vol. 5367, May 2004 (May 2004) pp. 302-311 XP-002512099.
Gering et al. An Integrated Visualization System for Surgical Planning and Guidance Using Image Fusion and Interventional Imaging Medical Image Computing and Computer Assisted Intervention—MIC CAI' 99 Lecture Notes in Computer Science, LNCS, Springer, Berlin, DE. vol. 1679, Jan. 1, 2006 (Jan. 1, 2006) pp. 809-820 XP019036236 MIT AI Laboratory, Cambridge MA, USA Bringham & Women's Hospital, Harvard Medical School, Boston MA, USA.
Torsen Butz et al. Pre-and Intra-operative Planning and Simulation of Percutaneous Tumor Ablation Medical Image Computing and Computer Assisted Intervention Ã MICCAI 2000 Lecture Notes in Computer Science, LNCS, Springer, Berlin, DE. vol. 1935, Feb. 11, 2004 (Feb. 11, 2004), pp. 317-326, XP019001272.
Nakao M et al. Haptic reproduction and interactive visualization of a beating heart for cardiovascular surgery simulation International Journal of Medical Informatics, Elsevier Scientific Publishers, Shannon, Ireland, vol. 68, No. 1-3 Dec. 18, 2002.
Franck P. Vidal "Simulation of image guided needle puncture: contribution to real-time ultrasound and fluoroscopic rendering, and volume haptic rendering" pp. 1-230 Thesis submitted in Candidature for the Degree of Doctor of Philosophy, Bangor University, UK Jan. 2008.
International Search Report for International Application No. PCT/IL12/00040 dated May 14, 2012.
V. I. Pokrovskiy. "An encyclopedic dictionary of medicinal terms", Moscow, "Meditsina", 2001, p. 613 (with translation of Russian Office Action which cites to this reference on p. 3).
Russian Office Action issued for application 2013137406 dated Jan. 18, 2016.

* cited by examiner

*Primary Examiner* — Anna Skibinsky
(74) *Attorney, Agent, or Firm* — Pearl Cohen Zedek Latzer Baratz LLP

(57) ABSTRACT

Embodiments of the invention are directed to a method of performing computerized simulations of image-guided procedures. The method may comprise receiving medical image data and metadata of a specific patient. A patient-specific digital image-based model of an anatomical structure may be generated based on the medical image data and the metadata. A computerized simulation of an image-guided procedure may be performed using the digital image-based model and the metadata.

20 Claims, 3 Drawing Sheets

SYSTEM AND METHOD FOR GENERATING A PATIENT-SPECIFIC DIGITAL IMAGE-BASED MODEL OF AN ANATOMICAL STRUCTURE

BACKGROUND OF THE INVENTION

Many invasive medical procedures such as for example endovascular procedures can pose challenges even to the most experienced physicians. Tortuous anatomy, difficult visualization, complex lesion morphology, and other complications can add to increased procedure time, fluoroscopy exposure, and contrast dye use. Precious time can be lost if the access strategy or equipment choice is suboptimal. Accordingly, simulation systems for image-guided procedures for training a physician without unnecessary risk, which may serve as pre-operative planning tool or post-operative assessment tool, have been introduced.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1:
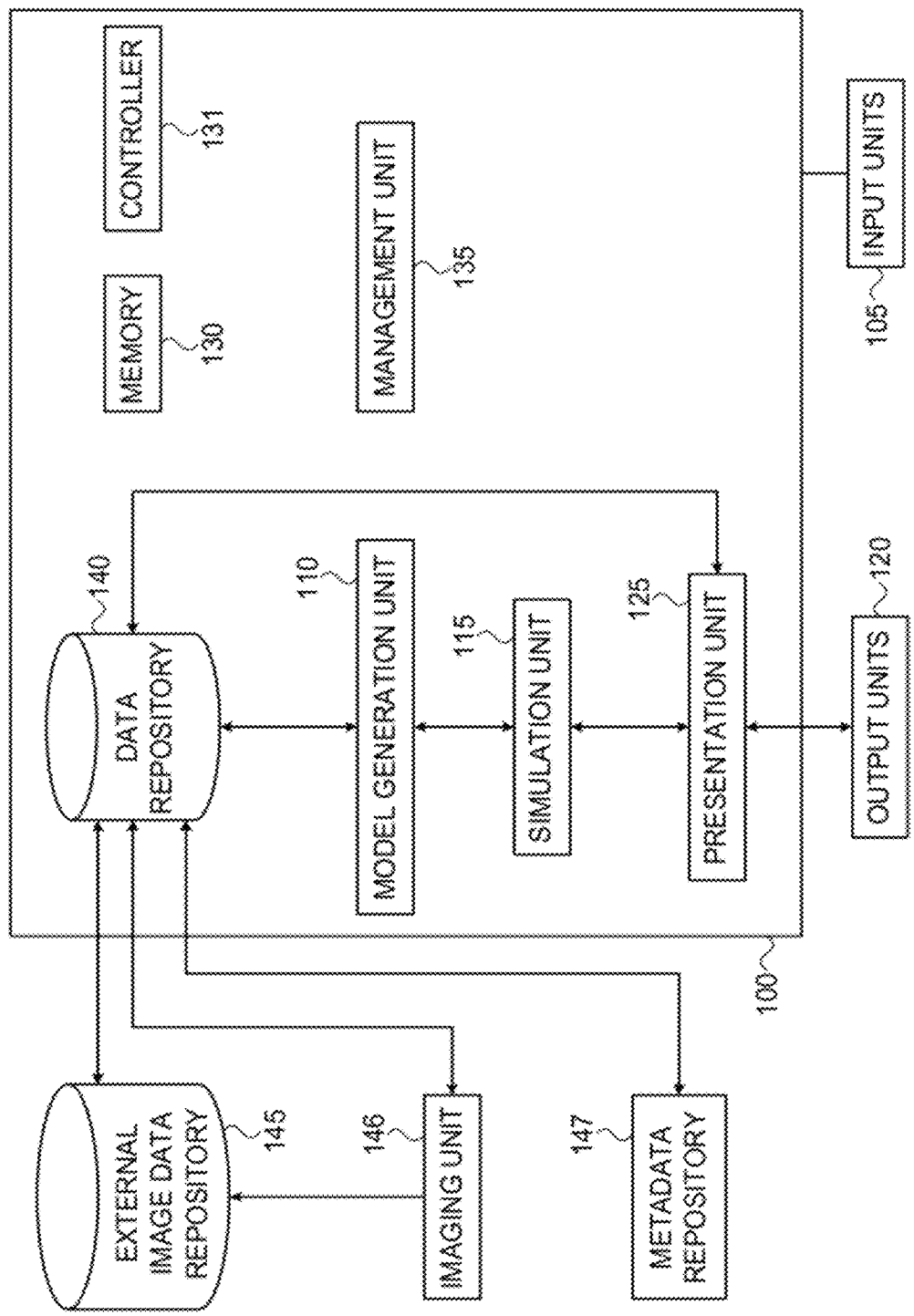
FIG. 1 shows an exemplary system for simulating an image-guided procedure according to embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those having ordinary skill in the art that the invention may be practiced without these specific details. In other instances, well-known methods, procedures, components, modules, units and/or circuits have not been described in detail so as not to obscure the invention.

Embodiments of the invention are directed to generating a digital, image-based, model of an anatomical and/or physiological structure based on medical image data and patient specific metadata. An anatomical and/or physiological structure may be and organ, tissue or vessel, e.g., a blood vessel, a heart, a bone or any applicable region, section or (possibly internal) part of a subject. Some embodiments of the invention are directed to generating a digital, image-based, model that exhibits, simulates or is otherwise related to a physiological behavior based on medical image data and patient specific metadata. A physiological behavior of a digital model may be based on metadata. For example, a digital model related to a specific patient may simulate or be otherwise related to a physiological behavior of the specific patient based on metadata related to the specific patient. For example, an interaction with medical tools, a reaction to a drug, a reaction to events of a specific patient may all be simulated, exhibited and/or performed by a digital model. Simulating a physiological behavior may include, for example, blood vessel elasticity, rate of blood flow, response to certain drugs or different drug dosage, bone strength, rapture probability, sensitivity to radiation, vessel reaction to various balloon inflation pressures etc. Accordingly, embodiments of the invention may be used for a number of purposes. For example, in order to enable a performance of a simulated procedure that may be used for training of physicians, research, or demonstrating a procedure.

Embodiments of the invention may enable producing a patient-specific digital image-based model of an anatomical and/or physiological structure based on medical image data received from a scan of a subject and further based on metadata of the patient that may be obtained or received as known in the art, e.g., in a digital imaging and communications (DICOM) image header. The subject may be, for example a patient that is about to undergo an image-guided procedure. According to embodiments of the invention, the medical images or other data may be patient-specific medical images and parameters obtained from the patient. For example, the medical images or other data may be obtained from a specific patient and provided to embodiments of the invention by one or more imaging systems such as computed tomography (CT), a CT-fluoroscopy, fluoroscopy, magnetic resonance imaging (MRI), Ultrasound, positron emission tomography (PET) and X-Ray systems or any other suitable imaging systems. Embodiments of the invention may use as input medical image data described herein to produce a 2D, 3D or 4D model of an anatomical structure, organ, system or region.

According to embodiments of the invention, a method of generating a digital, image-based model of an anatomical structure may include receiving and incorporating or otherwise using, any data, parameters, metadata or other information related to a patient. For example, any information or metadata related to a medical history or condition of a patient, known diseases, allergies, sensitivity to drugs and the like may be regarded as metadata and used by embodiments of the invention in a generation of a digital image-based model of an anatomical and associated physiological structure of the patient. Other metadata may be diagnostic information and/or opinions produced by one or more physicians, test results, results from various systems, e.g., a radiology system. For example, based on medical conclusion and diagnosis of a radiologist, specific sections of a digital image-based model may be enhanced. For example, the resolution of a specific section, area or organ may be enhanced, e.g., by producing or synthesizing additional, artificial information such as artificial CT slices, synthesized X-Ray images or other medical image data as described herein. In a particular case, based on the radiologist diagnosis of percent of plaque occlusion (e.g., total occlusion in the right internal carotid), the image-based model can be generated to reflect any aspects related to plaque occlusion, possibly in a specific location.

According to embodiments of the invention, a simulated procedure may be based on metadata. A digital image-based model may be manipulated according to relevant or related metadata. For example, various attributes, behavioral aspects or other parameters of a digital image-based model may be according to, or based on, metadata such as age, gender, medical condition or any applicable metadata related to the specific patient in addition to the medical images described herein. For example, behavioral aspects of a digital model, e.g., interaction with a simulated medical tool or reaction to an administered drug exhibited by a digital model may be according to or based on metadata as described herein.

For the sake of simplicity and clarity, any parameters, data or information other than image data received from an imaging system as described herein may be referred to herein as "patient metadata" or simply as "metadata" in order to distinguish such data from image data. Accordingly, age, gender, weight, height, life style, smoking or other habits, medical history or condition, known diseases or allergies as described above, or any such relevant or applicable information may be referred to herein as "patient metadata" or simply "metadata". As described herein, embodiments of the invention may provide a user with various views of images and other medical data. In some embodiments, an image may be generated based on received raw medical image data, artificially generated medical image data, metadata or a combination of metadata, raw and artificial medical image data. For example, artificial data may be a CT slice or image generated or synthesized by examining CT received from a CT system. In some embodiments, an image related to a specific surface, point of view or imaging system may be generated based on received raw medical image data, artificially generated medical image data and/or metadata. For example, based on metadata indicating a specific point of interest, an image may be generated or displayed. For example, metadata indicating a specific organ may require special attention may cause embodiments of the invention to generate an image where the specific organ may be best viewed.

In a particular scenario, a 3D digital image-based model may be generated based on input from a CT system as described herein. An X-Ray view may then be generated based on the digital image-based model and in correlation with metadata such that a specific region or organ is best viewed. For example, a two dimensional (2D) X-Ray view may be produced by projecting a three dimensional digital image-based model on a two dimensional surface or plane such that a specific organ is best viewed by a user. Embodiments of the invention may enable a user to select an X-Ray camera view, position or location with respect to a patient and produce an X-Ray image or view that would have been provided by an X-Ray camera located at the selected location and/or position. Accordingly, artificial or synthesized X-Ray images or views may be generated and provided even when no actual X-Ray camera is utilized for obtaining such images. Accordingly, based on metadata indicating a specific organ or region require special attention, a user may request and/or be provided with X-Ray like images of a region or organ of interest.

In an exemplary embodiment, data received from a CT system may be used to generate a digital image-based 3D model and such model may further be used to generate a view that would have been provided by a camera fitted, for example, on a colonoscope used for examination of the colon. Accordingly, in such exemplary embodiment, views revealing internal aspects or views of the colon may be generated and displayed. Likewise, views or images related to any applicable technology or system may be produced based on a digital image-based model. Accordingly, based on metadata a physician or a system may have prior to a generation and/or display of an image-based model, the physician may request and/or be automatically provided with views that enable the physician to view specific regions or organs of interest. In some embodiments, based on metadata, specific views (e.g., X-Ray like or internal views as described herein) may be automatically generated. For example, based on metadata indicating a patient suffers from an inflammatory disease of the intestines, views revealing internal aspects or views of the colon as described above may be generated and displayed.

The ability to generate views or images normally produced by various systems may be highly appreciated by those of ordinary skill in the art. Advantages of such ability may include a substantial saving of cost and time since based on metadata and data received from a first imaging system, embodiments of the invention may provide output related to a second, different system that may reveal aspects of interest as described herein. Accordingly, the ability to synthesize and provide images related to any angle, orientation, position or location of a simulated imaging device in accordance with metadata may be highly appreciated in the industry as they may enable a physician to effectively examine regions, organs or other aspects of interest. In some embodiments, artificial views as described herein may be displayed in addition to, or instead of, an image-based model generated based on raw image data as described here.

As described herein, displaying of metadata may be integrated or coordinated with, or otherwise related to a presentation, a progress or other aspects of a simulated procedure. In some embodiments, presentation of metadata may be according to a selection of a user. For example, a user may click a location on a simulated model, or otherwise select or indicate an interest in a location, anatomical organ or region related to the simulated model and be provided with relevant metadata. In other embodiments, presentation of metadata may be automatically synchronized or otherwise coordinated with a progress, state, mode or context of a simulated procedure. For example, metadata related to a location of a catheter, a wire, a stent or another simulated tool that may be shown in a simulated procedure may be automatically displayed.

In some embodiments, as a simulated medical tool is moved from a first location to a second location, a first displayed metadata may be automatically replaced by a second metadata (related to the second location) such that metadata related to the second location is presented instead of metadata related to the first location. Accordingly, a presentation of metadata may be automatically synchronized, matched and/or coordinated with a simulated procedure. For example, recent test results related to a patient suffering from an inflammatory disease of the intestines may be displayed upon selecting, or clicking on, the intestines in a simulated model. In another embodiment, real X-Rays of an anatomical organ may be displayed when a simulated medical tool is brought close to the related simulated anatomical organ.

Reference is made to FIG. 1 showing an exemplary system 100 for generating an image-based digital model of an anatomical region. Exemplary system 100 may further be used for simulating an image-guided procedure according to embodiments of the invention. As shown, system 100 may comprise a computing device comprising a number of units and operatively connected to input and/or output (I/O) units. System 100 may include input units 105, output units 120, a model generation unit 110, a simulation unit 115, a management unit 135, a data repository 140, a presentation unit 125, a memory 130 and a controller 131. Input units 105 may include a network interface card (NIC) e.g., enabling system 100 to communicate with a PACS system, a mouse, a keyboard, a touch screen or pad or any suitable input devices. Input units 105 may comprise means for operating simulation tools and tracking the user's manipulation of such tools. For example, physical objects such as handles, activation buttons and the like, as well as real or mock medical tools may be connected to input units 105 to enable a user to operate simulated tools such as a simulated catheter, suturing device, surgical scalpel, scissors, endoscope etc.

Additionally or alternatively, input units 105 may include a wired or wireless network interface card (NIC) that may receive data, for example, from an imaging system and may store obtained data, information or parameters in local data repository 140. According to some embodiments, a mediator unit, e.g., a communication management unit may utilize a NIC to communicate with a system or server storing medical images such as a picture archiving communication system (PACS), may obtain any relevant imaging information, data or parameters from such a system, server or application and may store obtained data, information or parameters in local data repository 140. Output units 120 may include display screens, speakers, components for interfacing with a display screen to enable visual output or optionally a speaker or another audio device to enable audible output. Output units 120 may include one or more displays, speakers and/or any other suitable output devices. Output units 120 may additionally include force feedback components that may apply, cause or generate physical forces or resistance (e.g., friction like resistance) to physical input devices that may be operated or manipulated by a user. Output units 120 and input units 105 may communicate with any other component or units of system 100 and accordingly may enable such units to communicate with external systems. Units 105, 110, 115, 125 and 135 may be or may comprise software, hardware, firmware or any suitable combination thereof. Output units 120 may enable communicating data to external repositories, For example, a procedure plan may be communicated via output units 120 to external image data repository 145, external metadata repository 147 or any other system that may store a procedure plan.

Also shown in FIG. 1 are an external image data repository 145, an external metadata repository 147 and an imaging unit 146. External image repository 145 may be any suitable or applicable database, repository or archive. For example, external image data repository 145 may be a picture archiving and communication systems (PACS) archive or repository. As known in the art, a PACS system may comprise computing and/or other devices that may be dedicated to the storage, retrieval, distribution and presentation of medical images. Images in a PACS system may be stored according to various formats, e.g., DICOM. A PACS system typically comprises or is operatively connected to an archiving system for archiving data such as CT, MRI or other images and related data, a secured network for the transmission of patient sensitive or private information and possibly, computing devices to receive image or other data from the archiving system. Embodiments of the invention may be configured to interact with a PACS system, e.g., over a network interface card (NIC) connected to a network such that communication with a PACS system is enabled. External metadata repository 147 may be any suitable or applicable database, repository or archive. For example, external metadata repository 147 may be a PACS archive or repository as described herein. In some embodiments, the same PACS, repository or database system may be used to implement or facilitate both external metadata repository 147 and external image repository 145. In some embodiments, external metadata repository 147 may be combined with external image data repository, e.g., in a PACS system or a DICOM system.

According to embodiments of the invention, a system (e.g., system 100) any interact with any applicable or suitable system in order to receive or otherwise obtain data or metadata or in order to send (e.g., for storage) information or metadata. Information stored according to any standard or protocol may be obtained from any system that may be interacted with over a network or directly connected to a system such as system 100. Embodiments of the invention may send and/or receive information according to any standard or protocol. For example, health-care patient records, data or metadata may be stored (e.g., by an external system or by system 100), sent or received by a system according to embodiments of the invention according to protocols such health level seven (HL7), electronic data interchange (EDI) or health informatics service architecture (HISA).

Management unit 135 may interact, e.g., over a network and possibly according to and/or by implementing a predefined protocol, with external data repository 145 that may be a PACS system. CT, MRI or other images and related data may be thus retrieved, received or otherwise obtained from such PACS or other system and may further be used as described herein and/or stored or buffered, for example, in data repository 140. Management unit 135 may interact, e.g., over a network or over a direct connection such as a communication bus, with external metadata repository 147 to retrieve any relevant, applicable or required metadata. For example, parameters, data or information such as age, gender, weight, height, blood pressure, heart rate or any other vital signs, exercise habits, medical history and/or tests results, family history, smoking habits, known diseases, allergies, sensitivity to drugs, X-ray or other images of various regions or any medical records that may be available may all be obtained from external metadata repository 147. It will be understood that for the sake of simplicity and clarity, a single external metadata repository 147 is shown in FIG. 1. However, system 100 may interact with any number of metadata repositories in order to obtain any relevant, applicable or required metadata.

In some embodiments, metadata repository 147 may interact with other repositories, e.g., in other medical facilities, in order to obtained metadata. In yet other embodiments, metadata may be provided to metadata repository 147 and/or system 100 by means of a removable storage device and media such as a compact disc (CD) that may be connected to metadata repository 147 or otherwise connected to system 100. Accordingly, embodiments of the invention are not limited by the type, nature or other aspects of a source of metadata nor by the way such metadata is communicated and/or received. Management unit 135 may interact with any component of system 100 and may coordinate operations of system 100. For example, management unit 135 may coordinate operations of data repository 140 and external data repositories such as external image data repository 145, imaging unit 146 and metadata repository 147, e.g., in order to enable data repository 140 to receive any required data from external repositories.

Imaging unit 146 may be an imaging system such as computed tomography (CT), a CT-fluoroscopy, fluoroscopy, magnetic resonance imaging (MRI), Ultrasound, positron emission tomography (PET) and X-Ray systems or any other suitable imaging system. As shown, medical image data and/or related data may be received by external image data repository 145 from imaging unit 146. External repository 145 may receive medical imaging data from any other applicable source, e.g., over a network from a remote site or hospital or by means of a removable storage device that may be connected to repository 145. As shown, system 100 may receive image data and/or related data directly from imaging unit 146. Although not shown, system 100 may receive imaging and/or other data from any applicable source, accordingly, embodiments of the invention are not limited by the type, nature or other aspects of a source of medical imaging or other data nor by the way such data is communicated and/or received.

Model generation unit 110 may include components or modules for generating a digital model and its graphical representation, e.g., a 3D anatomical model of an anatomical structure, such as an organ, vessel system or any other area of interest within a body of a subject. The model may be generated by model generation unit 110 according to information received from an imaging system, for example, a medical image received from a CT system via input unit 105. It will be recognized that embodiments of the invention are not limited by the method or system for generating a digital image-based model of an anatomical structure, any methods or systems may be used for generating such model without departing from the scope of the invention. In addition to being generated based on image data, the model may be generated by model generation unit 110 according to metadata obtained as described herein and possibly stored in data repository 140. For example, based on the medical analysis and measurements, a more accurate model may be generated. Any measurement, result, parameter or other metadata obtained from a patient may be used in a generation of a model. For example, a measured diameter of various parts of a vessel may be used in a modeling of the vessel.

According to embodiments of the invention, a digital image-based model may be associated with various behavioral aspects. For example, simulation unit 115 may cause a model to behave or otherwise exhibit traits based on metadata. For example, the interaction of a model (or an organ in the model) with a simulated medical tool may be specific to a specific model. For example, in the exemplary case above, the model of the older patient having stiffer blood vessel walls may be react differently to a catheter than the younger patient's model, e.g., when the catheter is pressed against a blood vessel's wall in the older patient's model, the wall may not yield or bend as much as a similar wall in the younger patient model. A digital image-based model may be generated according to any other metadata, e.g., gender, weight, height, vital signs, exercise habits, medical history and/or tests results, family history, smoking habits, known diseases, allergies, sensitivity to drugs, X-ray or other images of various regions or any other medical, personal or relevant information Simulation unit 115 may include components for generating a simulation of an image-guided procedure. For example, when a user performs a simulation, for example as a pre-procedure for an image-guided procedure, using simulation unit 115, a graphical representation of a digital model (e.g., produced by model generation unit 110), and the simulation process may be displayed on a monitor that may be one of output units 120. A generation of a digital model of an anatomical organ, system, section or region (e.g., by model generation unit 110) and a simulation of a procedure (e.g., by simulation unit 115) may be according to methods, systems and/or other aspects as described in US Patent Application Publication US 2009/0177454. A generation of a digital model of an anatomical organ, system, section or region may be based or in accordance with metadata as described herein. Likewise, a simulation of an image-guided procedure may be based on, or according to, metadata. Simulation unit 115 may include components for generating a simulation of an image-guided procedure based on metadata. For example, a simulated model may be caused by simulation unit 115 to exhibit, include or have attributes or characteristics related to the relevant metadata. For example, a sensitivity or reaction to a (simulated) administration of a drug, an interaction with a simulated medical tool or any other aspects or behavior of a simulated model may be according to or based on metadata of the relevant patient.

Controller 131 may be any suitable controller or processing unit, e.g., a central processing unit processor (CPU). Memory 130 may be any suitable memory component, device, chip or system and may store applications or other executable codes that may be executed by controller 131 and/or data, e.g., data that may be used by applications or programs executed by controller 131. For example, executable code, applications or modules implementing model generation unit 110 and/or simulation unit 115 may be loaded into memory 130 and executed by controller 131.

It will be recognized that system 100 as described herein is an exemplary system. According to embodiments of the invention, system 100 may be implemented on a single computational device or alternatively, in a distributed configuration, on two or more different computational devices. For example, model generation unit 110 may operate on a first computational device and managed by a first management unit whereas simulation unit 115 may operate on another computational device and managed by a second management unit that communicates with the first management unit. In another exemplary embodiment, management unit 135 may operate on a computational device, model generation unit 110 may operate on a second computational device and simulation unit 115 may operate on a third computational device.

Presentation unit 125 may control, coordinate or manage a display or presentation of video, audio or other aspects of a simulated procedure and related medical image data and metadata. For example, presentation unit 125 may receive data, parameters or other information from a plurality of sources and incorporate received or obtained data into a presentation to a user. Presentation unit 125 may coordinate, synchronize or otherwise relate a presentation of information from a plurality of sources within a single presentation.

For example, presentation unit 125 may coordinate or synchronize a presentation of metadata, e.g., a display of patient metadata as described herein may be coordinated or performed simultaneously with a presentation and/or performance of an image guided simulated procedure. Alternatively or additionally, presentation unit may cause a presentation of metadata according to a user selection. For example and as further described herein, a selection of a region of interest may be received from a user and a presentation of relevant metadata may be according to such selection. Management unit 135 may interact with any module, unit, application or other applicable entity and may perform coordination, scheduling, arbitration, supervising and/or management of flows, procedures or other aspects as described herein. For example, presentation unit 125 may coordinate or synchronize a presentation of a procedure plan.

Figure 2:
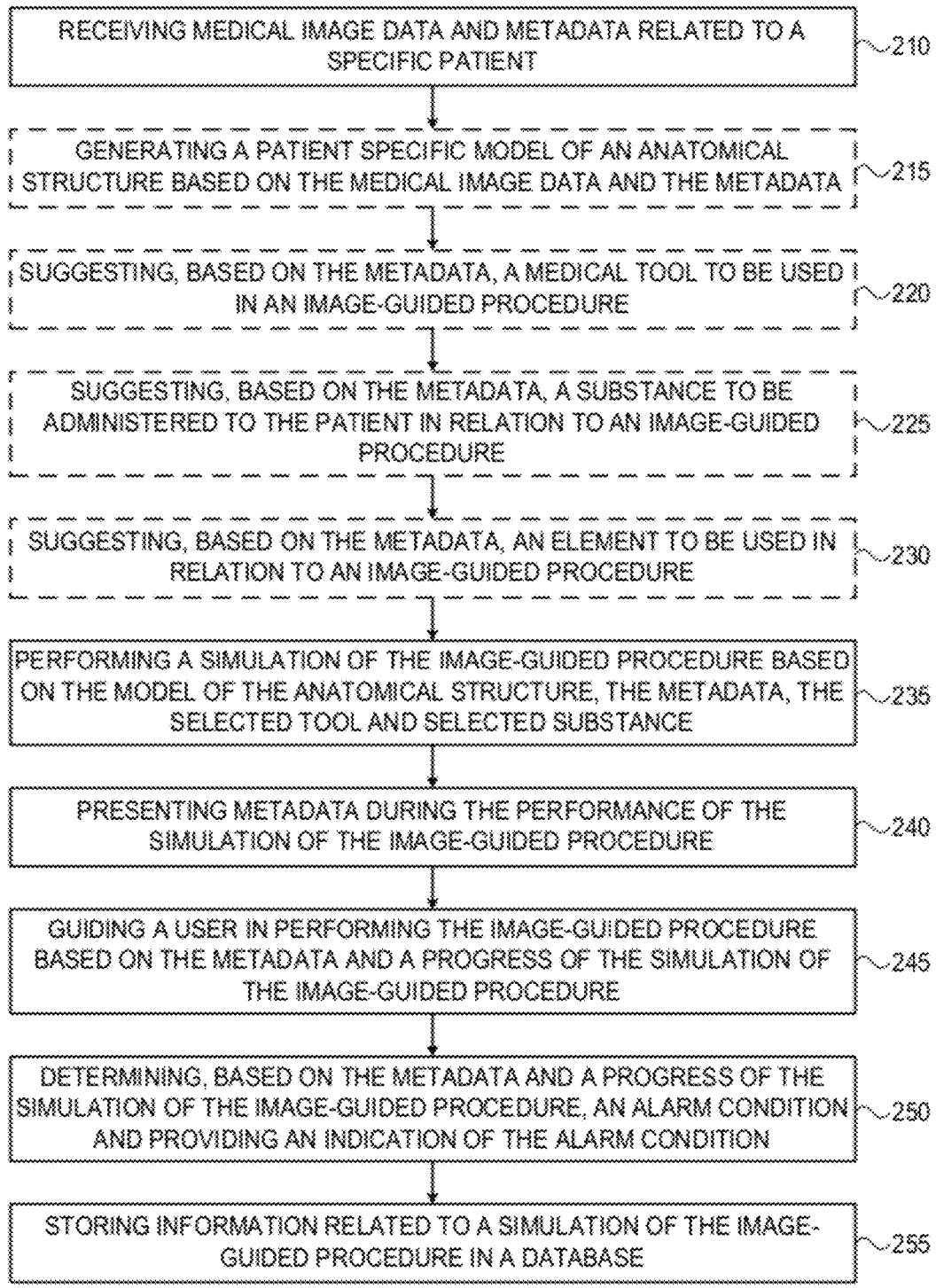
FIG. 2 is a flowchart diagram illustrating a method for simulating an image-guided procedure based on patient metadata according to some embodiments of the present invention.

Reference is made to FIG. 2, which shows an exemplary flowchart describing a method for generating a patient-specific digital image-based model of an anatomical structure and simulating an image-guided procedure according to some embodiments of the invention. The method may include receiving medical image data and metadata related to a specific patient that may be related to a specific subject or patient about to be treated (box 210). The medical image data may be received directly from an imaging or scanning system such as for example, a CT or MRI scanner or alternatively from an external image data repository, such as a picture archiving communication system (PACS). As will be understood to a person skilled in the art, the medical image data may be received from any other applicable source. The metadata may be received directly from a metadata repository, database or any other source, e.g., metadata repository 147 described herein. As will be understood to a person skilled in the art, the metadata may be received from any other applicable source According to some embodiments, the received medical data and metadata may be stored locally or internally within a data repository, such as data repository 140. According to some embodiments, possibly based on received data, data may be generated. For example, based on a set of three hundred (300) CT images and metadata as described herein, an extended set of six hundred (600) may be generated. For example, by examining an initial set of images and by further examining metadata related to the specific patient, embodiments of the invention, e.g., executable code executed by controller 131, may generate or produce additional images and thus produce a new set of images. For example, if a given set of images was produced by acquiring a single image per a movement of one centimeter (1 cm) of the imaging unit, a new set may be produced by artificially generating images to reflect a movement of half a centimeter (½ cm) of the imaging unit.

In some embodiments, based on two sequential images in an original set and further based on metadata as described herein, an additional image may be artificially generated, e.g., by observing variations between the two original images and by further observing various aspects reflected by relevant metadata. For example, based on metadata as described herein, embodiments of the invention may generate artificial images of a specific area of interest. For example, based on metadata indicating a specific disease or condition, related regions may require higher resolution. Accordingly, based on metadata, additional artificial images may be generated in order to provide better view of specific regions. Such metadata based generation of images or other medical image data may be automatic or it may be based on a user selection. For example, having studied metadata of a patient, a physician may determine a higher resolution of a specific region in a generated model is required. In such case, the physician may select regions to be generated with such higher resolution, or have such regions modeled based on a higher number of images. Based on such selection, additional or artificial images may be generated as described herein.

In other embodiments, generation of artificial images based on metadata may be automatic. For example, system 100 may be configured to automatically generate additional images, or ascertain a minimum number of images per specific region is available based on a specific parameter, value or other criteria related to a metadata of a patient. For example, metadata indicating a heart possible condition may cause generation of additional artificial images such that at least a resolution reflecting a movement of a quarter of a centimeter (¼ cm) of the imaging unit is achieved for the heart or a specific region around the heart in the digital model. Any other rules or criteria may be likewise configured in relation to any metadata and/or modeled regions or anatomical organs.

An artificially generated image may be inserted between two relevant original images in order to produce a new set of images that may be coherent and may adequately represent the anatomy or other aspects of a related patient. Such generation of images may enable embodiments of the invention to provide better resolution, and enhance a correlation of medical data and a simulated procedure as described herein. Such generation of images based on metadata may enable embodiments of the invention to provide selective resolutions based on metadata thus provide, possibly automatically, higher resolution for specific regions of interest based on a medical condition or other aspects of a patient as reflected by the relevant metadata described herein. Since metadata available to embodiments of the invention as described herein may relate to highly relevant medical aspects of the patient, automatically, selectively and/or otherwise generating additional or artificial images based on metadata, thus automatically and/or selectively increasing a resolution and/or accuracy of selected regions or anatomical organs in a model, may be a highly appreciated aspect of the present invention. A set of images, either as received or extended as described herein may be stored locally, e.g., in data repository 140.

As described herein, raw medical image data, e.g., acquired by, and received from an imaging system may be processed. Processing of medical image data may be performed prior to generating views or image based models as described herein. For example, pixels for rendering may be produced by interpolation applied to acquired pixels or other image related data. For example, CT slices may be artificially generated by interpolation of acquired CT slices. Windowing transformations as known in the art may be another example of processing that may be applied to medical image data by embodiments of the invention, e.g., in order to enhance, alter or otherwise modify aspects such as contrast or brightness of an image that may be received from an imaging system or may be artificially generated as described herein. Any such processing may be based on metadata. For example, aspects such as contrast or brightness of a specific region or anatomical organ may be enhanced or altered based on metadata. For example, a known disease may be known to affect a specific region or anatomical organ. Accordingly, based on an indication of such disease (or a possibility of such disease) in metadata of a patient, the contrast or brightness of the likely to be affected region or organ may be increased. In some embodiments, DICOM tags may be used. For example, DICOM tag name "WindowCenter" (0028, 1050) and/or DICOM tag name "WindowWidth" (0028,1051) may be used in setting thresholds for a segmentation process or other operations related to generating a patient-specific digital image-based model As shown by box 215, the method may include generating a patient specific model of an anatomical structure based on the medical image data and the metadata. Generation of an anatomical structure may be based on examining and/or processing of medical data and metadata, e.g., as received as shown by box 210 and/or generated as described herein. In cases where the imaging data is patient specific, e.g., is produced by imaging or scanning a real specific patient or is extended based on specific patient image data and metadata, the anatomical model may be patient specific too, namely, the model generated as described herein may represent a specific, real patient. Model generation may be according to methods or other aspects as described in US Patent Application Publication US 2009/0177454. As further described herein, the digital model may be generated based on metadata. A patient specific model of an anatomical structure may be generated based on any metadata related to the patient, e.g., medical history, physician's diagnosis or opinion, medications the patient may be taking, etc.

For example, based on previous examinations, plaque type in a patient's blood system may be known or deduced based on the patient's metadata, and the simulated model may be according to such known or deduced plaque type. A plaque type may effect a simulation of a procedure. For example, if the plaque percentage of a stenosis is 60%, then the generated model may reflect such percentage. Metadata related to lesions may be another example of metadata that may be used in a generation of a model and/or performance of a simulated procedure as described herein. In some embodiments, a specific organ in a model may be generated or modeled based on metadata. For example, incomplete information may be supplemented using metadata. For example, data received from an imaging system may only suffice in order to model a section of an organ, e.g., a blood vessel, but may be insufficient in order to model the entire vessel, or an additional section of the vessel that may be required. In such exemplary case, based on metadata identifying a specific organ as a blood vessel, model generation unit 110 may extend the blood vessel, e.g., by extrapolation, such that a sufficient portion of the blood vessel is modeled. In other cases, pathologies or other phenomena may be modeled based on metadata. For example, a lesion in a blood vessel, a deformation of an organ or other aspects may be modeled based on metadata even if they are not reflected in imaging data, e.g., not reflected in CT images obtained from the patient.

As shown by box 220, the method may optionally include suggesting, based on the metadata, a physical medical tool to be used in an image-guided procedure. For example, based on metadata a catheter model or type, a balloon type or size or a wire tip may all be suggested. As known in the art, different medical tools or medical tools types may be suitable to different patients and/or different patient conditions. For example, a first catheter may be suitable for a young male patient suffering from a first illness or condition, a second catheter may be suitable for a young female patient suffering from a second illness or condition and a third catheter may be suitable for an old female patient suffering from a third illness or condition. Accordingly, based on an illness, medical condition or any aspect that may be determined from metadata, a medical tool such a catheter may be automatically suggested as shown by box 220.

As shown by box 225, the method may optionally include suggesting, based on the metadata, a substance or drug to be administered to the patient in relation to an image-guided procedure. For example, based on metadata, administering heparin (e.g., before deploying a balloon or stent) or nitroglycerin (e.g., when carotid spasm is simulated) and/or atropine (e.g., when specific blood pressure phenomena are simulated) may be automatically suggested by simulation unit 115. The type of drug suggested to be administered may be selected based on metadata.

As known in the art, different drugs or medications may be suitable for different patients and/or different patient conditions. For example, a first drug and/or dosage may be suitable for a young female patient suffering from a first illness or condition, a second drug and/or dosage, medication or substance may be suitable for a young male patient suffering from a second illness or condition and a third drug and/or dosage, medication or substance may be suitable for an old male patient suffering from a third illness or condition. Accordingly, based on an illness, medical condition and/or any aspect that may be determined from metadata as described herein, a drug, medication or substance or a type and dosage and/or rate of introduction thereof, e.g., a type, dosage and rate of administration of a sedative drug may be automatically suggested as shown by box 225. It will be understood that any aspects related to an introduction or administration of a drug or substance may be automatically suggested based on metadata as described herein. For example, the type and dosage of a drug or substance, rate and/or location of administration, or other means (e.g., intravenous or through the gastrointestinal tract) may all be suggested based on metadata as described herein. Such automation of a selection of a drug or substance to be administered as well as a method of administration and other aspects as described herein may save time and further help avoiding wrong decisions and may accordingly be a highly valuable feature or aspect of the present invention. It will be understood that a number of suggested medical tools, substances and/or methods of administration may be presented or displayed to a user who may select one of such number of suggested options.

According to some embodiments of the invention, an element to be used may be suggested based on metadata and/or a simulated model. In other embodiments, an element may be automatically selected based on metadata of a patient. For example, a first stent may be suggested for a young patient and a second stent, better suited for an older patient may be automatically suggested or selected based on the patient's age as indicated in metadata of the patient. Other elements may be selected based on a patient's metadata, e.g., an endograft used in abdominal aortic aneurysm (AAA) and/or thoracic aortic aneurysm (TAA) simulated procedures, a coil in a peripheral embolization simulated procedure, a clip to be used in an open neuro surgery simulated procedure or a sleeve to be used in an open abdominal surgery simulated procedure may all be automatically suggested or even automatically selected, e.g., by simulation unit 115, based on patient metadata.

According to embodiments of the invention, based on suggesting a medical tool or substance as shown by optional boxes 220 and 225 and 230, the method may include receiving a selection of a medical tool and of a substance to be administered and element to use. According to embodiments of the invention, the suggestions of a medical tool, substance or element as described herein may be made graphically, e.g., displayed on a display operatively connected to a computing device or controller, e.g., controller 131. Accordingly, a selection may be performed by interacting with a display (e.g., in the case of a touch screen) or using a point and click device and/or a keyboard as known in the art. For example, a user may click on one of a number of displayed suggested medical tools, elements, substances and/or methods of administration. In other embodiments, a medical tool, element and/or substance to be administered may be automatically selected based on metadata or other considerations, aspects or criteria. For example, based on the age of the patient, a catheter may be selected, e.g., a smaller catheter may be selected for a young patient while a larger catheter may be selected for an older patient. Likewise, a first drug best suited for a patient suffering from a specific first illness may be selected for administration while a second drug or medicament may be selected for a second patient suffering from a different second specific illness.

As shown by box 230, the method may optionally include suggesting, based on the metadata, an element to be used in relation to an image-guided procedure. For example, based on a patient's age, a stent type or size may be suggested. Other elements that may be suggested may be an endograft, a coil, a clip and/or a sleeve. Any parameters related to an element may be suggested. For example, a size, type, location or orientation of an element may all be suggested based on metadata data that may be an age, gender, medical history and/or a diagnosis of a physician, an indication of an element by a physician (that may have examined the patient in the past and indicated a preferred treatment and/or element)

As shown by box 235, the method may include performing a simulation of the image-guided procedure based on the model of the anatomical structure, the metadata, the selected tool, the selected element and selected substance. As described herein, a simulation of an image-guided procedure may comprise simulating any aspects of the related actual procedure. For example, a physician may operate medical tools, be provided with feedback by a force-feedback system and the digital model may be made to exhibit real life behavior, e.g., react to medical tools and/or administered drugs, assume states such as hyperemia or shock etc. Any aspect or behavior of the model and tools that may cause the simulated procedure to be as real as possible may be performed, e.g., by components of system 100 described herein. For example, controller 131 may cause a model to exhibit any real life or real patient behavior and/or reaction to a simulated medical tool and a simulated administration of drug or medicine.

According to embodiments of the invention, a simulated procedure may comprise a graphical representation of an anatomical model that may be displayed on a monitor with additional information, such as simulated models of (possible selected as described herein) medical or other tools. In some embodiments, the graphical representation of the anatomical structure or organ and of the tools and elements may exhibit real anatomical or physical qualities, traits, features, nature or aspects, e.g., move, bend, contract, react to pressure or medicine, bleed etc. As described herein, qualities, traits, nature or other aspects of a model may be based or according to metadata. For example, a model may exhibit aspects, or behave like, a specific patient suffering from a specific condition would. For example, a simulated heart rate, tendency to bleed, reaction to an introduced drug may all be according to metadata of the specific patient. A simulation of an image-guided procedure may comprise an image or graphical representation of an anatomical organ, e.g., a model as described herein, that may be rotated or otherwise positioned, or may be made to imitate a real anatomical system, e.g., change or evolve with time, change shape in response to an operation of, or an interaction with a medical tool or substance, bleed, or otherwise present or display real anatomical organ's behavior and related tools, elements, medicine or other aspects in accordance with the related metadata. For example, a catheter, stent or other tools, devices or elements may all be shown and further simulated. In cases where the medical image data and metadata used for generating a model as described herein is patient specific, the model generated as described herein may also be patient specific and, accordingly, a simulation of a procedure as described herein may be patient specific, namely, reflect, simulate or be otherwise related to a real procedure performed on a real, specific patient. Accordingly, a physician may perform a computerized simulation of the image-guided procedure as a pre-procedure of the actual surgery (e.g., a surgical rehearsal or surgical simulation), part of a planning procedure, as a training session or as a post-procedure.

As shown by box 240, the method may include presenting metadata during the performance of the simulation of the image-guided procedure. For example, presentation of related metadata may be performed simultaneously or concurrently with performance of a related simulation of an image-guided procedure, or it may be otherwise at the same time. In some embodiments, presentation of metadata may be synchronized or otherwise coordinated with a progress, state, mode, context or any relevant aspect of a simulated procedure. In cases where the metadata is related to a specific patient and, accordingly, the model and simulation described herein may be patient specific as well, patient specific metadata may be presented together with the simulated procedure, e.g., while the simulated procedure is in progress. For example, a single display may be used to present metadata and a simulated procedure at the same time, e.g., as shown in FIG. 3.

Figure 3:
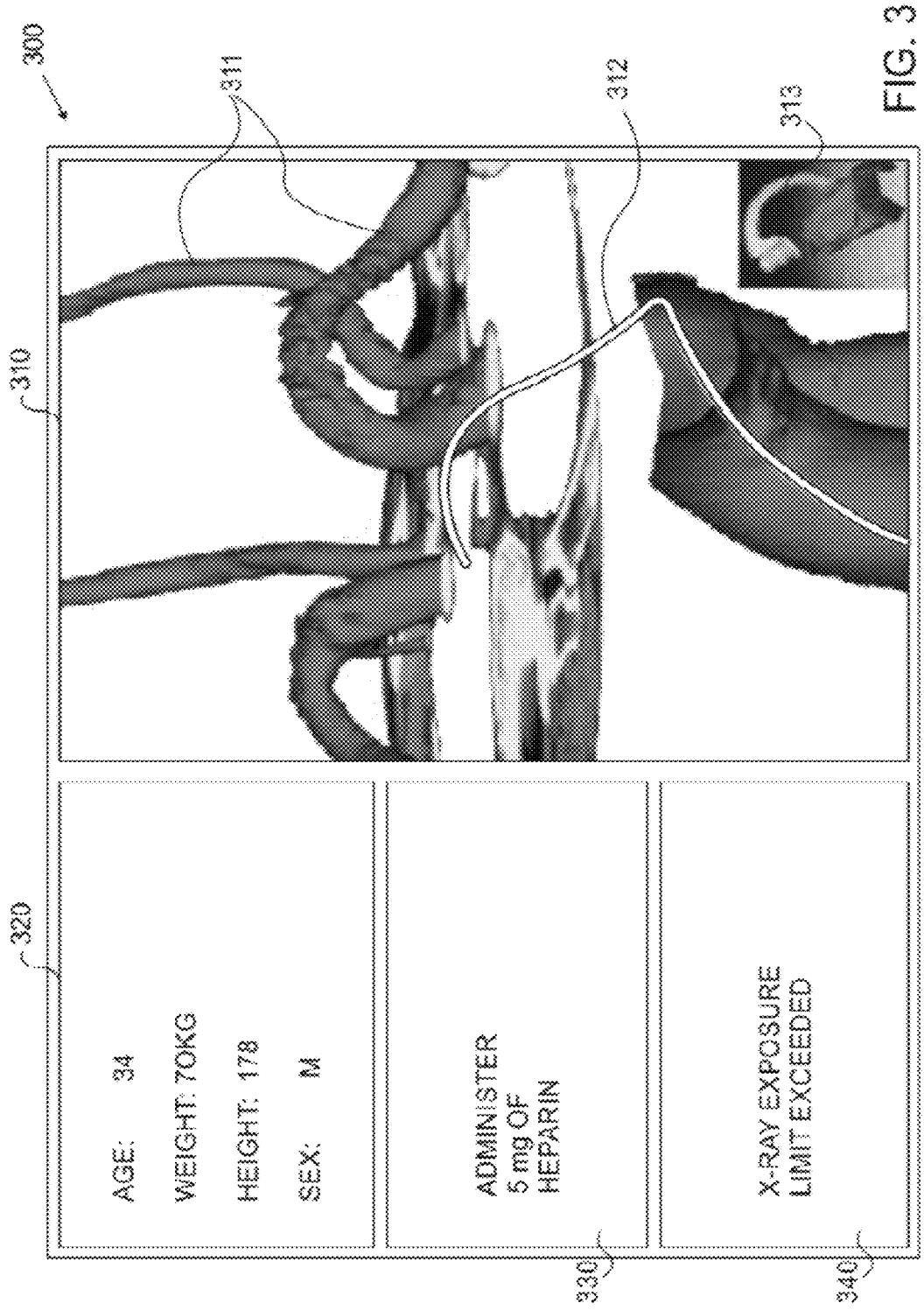
FIG. 3 shows an exemplary screenshot related to a presentation of a patient-specific digital image-based model of an anatomical structure and a presentation of related metadata.

Reference is additionally made to FIG. 3 showing an exemplary screenshot 300 related to an integrated presentation of a simulated medical procedure, metadata and/or other information according to embodiments of the invention. As shown by FIG. 3, a display may be divided into a number of regions, for example, four regions 310, 320, 330 and 340. A first region 310 may be related to the simulated procedure and may accordingly present a patient-specific digital image-based model of an anatomical structure. In this exemplary display, the image-based model represents a vessel. Region 310 may further display a simulated or virtual medical tool model representing a physical intervention medical tool manipulated by a user during a simulated procedure. For example, a catheter 312 may be shown with relation to blood vessels 311. A simulated procedure may comprise showing a movement of the catheter, e.g., as a result of actions taken by a physician, as well as reaction or other behavioral or other aspects of the anatomical organs and tools (e.g., based on metadata as described herein). For example, as the simulation progresses, catheter 312 may be shown to move through blood vessels 311, and blood vessels 311 may be shown to move, bend or otherwise react or exhibit phenomena typically seen or exhibited by real living organs. Such behavior of blood vessel 311 may be according to metadata as described herein. For example, a blood vessel 311 of a patient suffering from a disease known to cause highly calcified blood vessels may be made to bend or otherwise react differently to catheter 312 than blood vessel 311 of a healthy patient.

As shown by 320 in FIG. 3, a second region or area may be dedicated or related to presenting related metadata. For example and as shown, a patient's age, weight and other metadata information may be shown. As described herein, various information, presentation modes and other features may be enabled with respect to the presentation of metadata. For example, presentation of metadata in region 320 may be correlated or synchronized with a location of a simulated tool or part of a simulated tool that may be shown in the simulation region 310. For example, metadata related to a specific location or region may be displayed in region 320 when catheter 312 or the tip of catheter 312 is in close proximity to such specific location or region.

For example, metadata related to a first location may be presented in region 320 when the tip of catheter 312 is within a predefined distance from such first location. As the simulated procedure progresses and catheter 312 is moved to a second region or location, metadata related to such second location or region may be presented in region 320, for example, while the tip of catheter 312 is within a predefined distance from such second location. Correlation, synchronization, coordination and/or integration of a simulated model and/or procedure with a presentation or related metadata as described herein may be implemented and/or performed according to any applicable design or configuration. For example and as shown by FIG. 1, presentation unit 125 may interact with simulation unit 115 in order to obtain any relevant information or parameters related to a state, context, progress or other aspect of a simulation. Presentation unit 125 may further interact with data repository 140 (or any other applicable data repository) in order to obtain relevant metadata and further cause display of such metadata. Accordingly, possessing any relevant information related to the simulation and metadata, presentation unit 125 may coordinate, synchronize or otherwise relate a presentation of metadata with the simulated procedure.

For example, as the simulated model used for a simulated procedure may be generated based on metadata, the simulated model may include references to related metadata. As known in the art, cross references related to a number of objects, structures or elements may be used in order to relate digital elements, data objects or other structures to one another. For example, a specific region or volume of a simulated model may be generated based on, or in accordance with specific metadata as described herein. Accordingly, cross references related to elements in a simulated model and metadata information, parameters or elements may be maintained and used in order to correlate, coordinate, synchronize or otherwise relate a presentation of a simulated model and/or procedure with the relevant metadata. For example, presentation unit 125 may receive or obtain a reference to a metadata parameter (e.g., a specific value) based on which a model was generated (e.g., by model generation unit 110) and may use such reference to retrieve the relevant metadata parameter or value from repository 140 and further display metadata parameter as shown by 320. Any presentation combining an integrated presentation of metadata and a simulated model as described herein may be generated. For example (although not shown) rather or in addition to displaying metadata in region 320, metadata may be displayed in the simulation region 310. For example, using cross references as described herein, metadata related to a specific region or anatomical organ may be displayed near, on (e.g., in overlay mode) or close to the region or organ.

As shown by 330, a third region may be used for displaying instructions, suggestions or other guidance to an operator of system 100. Such guidance may be based on metadata. For example, based on metadata indicating a possible sensitivity of a patient to a specific drug, a suggestion to reduce the amount of such drug may be displayed in region 330. Another example may be a suggestion to increase a dosage or to administer a specific substance. For example, based on metadata it may be determined that the patient may require a blood diluting substance that may ease or help performance of the procedure. Accordingly, a suggestion to introduce a suitable medicament or substance may be presented in region 330.

According to embodiments of the invention, parameters to be monitored may be defined or selected. Conditional operations may be defined for, and associated with, monitored or tracked parameters. For example, simulated vital signs, e.g., a blood pressure or heart rate of a simulated model may be monitored. Alarm conditions or other criteria may be associated with monitored parameters. For example, according to a definition or a selection of a user, an alarm may be triggered when a heart rate signal generated by a digital model exceeds a predefined rate. Monitoring parameters, conditions or other aspects related to a digital model may be according to any criteria, rule, threshold, limit, amount, level or other quantity or parameter. Monitoring parameters may be performed in real-time, for example, a patient's vital sign may be monitored while a simulated procedure is in progress, e.g., as may be done during an actual (non-simulated) procedure. Indicating an alarm, and/or otherwise providing information related to tracked or monitored parameters may be done in real-time. For example, indicating an exposure duration time has been exceeded may be performed in real-time, during a simulated procedure. Any information related to monitored parameters may be stored. For example, a stored procedure plan may include values related to tracked parameters. For example, upon detecting an alarm condition, the time the alarm occurred (e.g., relevant time from the beginning of the procedure), the value, level or amount that caused the alarm condition and any other relevant information may be recorded, e.g., in a procedure plan. Other recording schemes may be possible, for example, recording information related to monitored parameters may be periodic, continuous or otherwise performed.

As shown by 340, a fourth region may be used for displaying alarms or other indications that may be generated based on metadata. For example, based on metadata one or more limits related to exposure to radiation may be computed. For example, maximum exposure duration and/or radiation intensity related to an old patient may not be the same as those related to a young patient. Other criteria, e.g., gender, sensitivity to drugs etc. may all be relevant to various aspects of the procedure. Accordingly, alarms, warnings or other indications may be generated based on the procedure and the metadata and may be displayed in region 340 as described. Other regions (not shown) may comprise user interface elements, e.g., graphical user interface (GUI) objects, that may enable a user to control various aspects of a simulated procedure and display of medical data as described herein. For example, various aspects, e.g., color of warnings, sound etc. may be selected or controlled, e.g., as known in the art. In other embodiments, other regions may be shown on a display. For example, a CT slice related to a location of a medical tool may be shown, e.g., in a separate region or overlaid on the model.

Presentation of metadata may be automatic, e.g., according to various constraints, conditions, event or other aspects related to a simulated procedure. In some embodiments of the invention, metadata may be automatically selected, presented, replaced or otherwise manipulated, e.g., based on a progress, state and/or context of a related to a simulated procedure. For example, a checkbox (not shown) may enable a user to select a mode of presenting metadata according to a location of a tool or part of a tool. For example, checking a "follow tip" checkbox may cause embodiments of the invention to update a presentation of metadata based on the location of a tip of a simulated catheter, e.g., the tip of catheter 312. It will be understood that other arrangements of regions 310, 320, 330 and 340 may be possible and/or user configurable. Accordingly, presentation of metadata may be according to a progress of a simulated procedure. Alternatively or additionally, metadata may be presented based on a selection of a location or region in the simulated model. For example, upon detecting a selection, e.g., a click of a mouse on a specific location or element of a simulated model, the relevant metadata may be displayed, e.g., in a dedicated region or area such as region 320 in FIG. 3. Accordingly, a physician may be presented with metadata with respect to a simulated model. Such presentation may be performed during a progress of a simulated procedure or in offline mode. For example, the physician may pause, stop or terminate a simulated procedure, examine the simulated model (that may be static or frozen), and further select to review metadata related to a specific location in the model, e.g., by clicking a location of interest on the model. Presenting metadata based on a selection of a location on a simulated model may be accomplished by utilizing cross references as described herein.

Referring back to FIG. 2 and as shown by box 245, the flow may include guiding a user in performing the image-guided procedure based on metadata and a progress of the simulated image-based procedure. For example, guidance may be provided in region 330 of FIG. 3 as described herein. As shown by box 250, the flow may include determining, based on the metadata and a progress of a simulation of an image-guided procedure, an alarm condition and providing an indication of the alarm condition. For example, various aspects of the simulated model (e.g., heart rate, temperature etc.) may be related to metadata and an alarm condition may be determined accordingly. For example, while a specific heart rate of an old patient may be determined to be too high or dangerous and cause an alarm to be generated and provided to an operator of system 100, the same heart rate, when the patient is a young child may not cause an alarm to be generated. Likewise, while a specific heart rate immediately after an introduction of a drug may be considered normal (e.g., if the drug is known to increase heart rate), the same heart rate may cause an alarm to be generated and displayed or provided if a specific time period has elapsed since introduction of the drug. Accordingly, alarms, warnings or other indications may be based, at least in part, on the relevant metadata and/or a progress of the simulated procedure.

As shown by box 255, the flow may include storing information related to the a simulation of the image-guided procedure in a database. For example, an entire simulated procedure, including metadata displayed, operator's actions, snapshots of the simulation and any information displayed or otherwise provided may be recorded and stored, e.g., on a PACS archive or any suitable or applicable database, repository or archive. Selection, suggestion and/or usage of tools, drugs and elements in a simulated procedure may be all be recorded and stored. For example, an entire simulated procedure and any relevant information, data or parameters may be stored as a procedure plan that may be used at a later stage in order to plan, or prepare for, a real procedure, e.g., a real procedure performed on the patient associated with the metadata.

For example, a procedure plan stored as shown by box 255 may include tools, elements and drugs suggested and selected during a simulated procedure so that any suggestion or selection made during a simulated procedure may be shown or indicated to a physician, e.g., by replaying the simulated procedure or by otherwise providing information in a stored procedure plan. Other parameters or data in a stored procedure plan may be a C-arm position, orientation or angulation, any relevant lesion data and/or a simulated image. A procedure plan may be stored in any storage. Generally, primary metadata or primary metadata storage as used herein may refer to metadata content or storage used for reading or obtaining metadata as well as writing or storing metadata. For example, a DICOM header may be used as a primary metadata storage by reading metadata from the DICOM header, e.g., in order to generate a digital model based on the metadata and writing metadata to the DICOM header (e.g., using a DICOM tag), for example, any results, comments or other information related to a simulated procedure or a procedure plan may be written to a DICOM header or other primary metadata storage or content. For example, a primary metadata storage (that may be or may be included in metadata storage 147) may store a procedure plan. In other embodiments, a PACS system may be used to store a procedure plan, e.g., in a DICOM header related to the specific patient.

A procedure plan may include any relevant aspect. For example, a position of an X-Ray camera, a route or navigation of a catheter, a tool selection, a drug used, an element (e.g., a stent type and properties) may all be recorded as part of a procedure plan. Any other information may be stored in association with a procedure plan. For example, any metadata or image data (e.g., one or more CT slices or images) may be stored as part of, or in association with, a procedure plan. Another example of data that may be part of a procedure plan may be an X-Ray view produced or synthesized from a digital image-based model as described herein. Generally, a procedure plan may be a plan for an upcoming procedure, may determine or suggest an approach, interventional tools, address potential complications, relate to aspects such as a C-arm position or angle (possibly for specific steps in a procedure), provide lesion view and data etc.

A stored procedure may, at any time, be loaded, e.g., into system 100 and replayed, e.g., for training, tutoring or other applicable purposes, e.g., a preparation for a procedure. In a particular embodiment, using DICOM, information may be stored in association with DICOM images or other objects, e.g., as metadata associated with DICOM information. By using a procedure plan, a real procedure may be improved, for example, exposure to radiation may be reduced and/or procedure time may be shortened as the physician may be better prepared for the real procedure by reviewing, replaying or other using the procedure plan. For example, a procedure plan may be presented (e.g., replayed) to a physician during a real or actual procedure.

Embodiments of the invention may include an article comprising a non-transitory computer-readable storage medium, having stored thereon instructions, that when executed on a computer, cause the computer to receive medical image data related to a specific patient, receive metadata related to the specific patient and generate a patient-specific digital image-based model of an anatomical structure of the specific patient based on the medical image data and the metadata. When executed on a computer, the instructions may cause the computer to perform a computerized simulation of an image-guided procedure using the digital image-based model and the metadata and manipulate the digital image-based model based on the metadata. An article according the embodiments of the invention may be or include units, modules, components or elements such as a computer or processor non-transitory readable medium, or a computer or processor storage medium, such as for example a memory, a disk drive, or a USB flash memory, encoding, including or storing instructions, e.g., computer-executable instructions, which when executed by a processor or controller, carry out methods disclosed herein.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like.

Unless explicitly stated, the method embodiments described herein are not constrained to a particular order or sequence. Additionally, some of the described method embodiments or elements thereof can occur or be performed at the same point in time or overlapping points in time. As known in the art, an execution of an executable code segment such as a function, task, sub-task or program may be referred to as execution of the function, program or other component.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

What is claimed is:

1. A method of simulating an image-guided medical procedure, the method comprising:
   receiving, by a computing device, medical image data related to a specific patient;
   receiving, by the computing device, medical history metadata related to health-care patient records of the specific patient, the medical history metadata not including the medical image data; and
   generating, by the computing device, a patient-specific digital image-based model of an anatomical structure of the specific patient based on the medical image data and the medical history metadata, wherein the patient-specific digital image-based model exhibits a simulated patient-specific physiological behavior based on the medical history metadata, and the simulated patient-specific physiological behavior includes any of an interaction, reaction or response;
     wherein the patient-specific digital image-based model comprises a three-dimensional (3D) anatomical model of an anatomical structure; and
     wherein the patient-specific digital image-based model is displayed on a display; and
   using the patient-specific digital image-based model in a simulation of the image-guided medical procedure, the simulation comprising applying a force feedback to a physical medical tool operated by a physician using the simulation, the simulated patient-specific physiological behavior including that the patient-specific digital image-based model's interaction with the physical medical tool is based in part on the medical history metadata.

2. The method of claim 1, comprising manipulating the digital image-based model according to the medical history metadata.

3. The method of claim 1, comprising:
   suggesting, by the computing device, based at least in part on the medical history metadata, at least one physical medical tool to be used in the image-guided procedure;
   receiving, at the computing device, a selection of a physical medical tool from a user; and
   providing a simulated model of the selected physical medical tool, wherein the simulation comprises manipulating the simulated model of the selected physical medical tool, and the simulated patient-specific physiological behavior comprises an interaction with the simulated model of the physical medical tool according to the medical history metadata.

4. The method of claim 1, comprising:
   suggesting, based at least in part on the medical history metadata, a dosage of a substance to administer; and
   receiving a selection of a dosage of a substance, wherein the simulated patient-specific physiological behavior comprises a reaction to the selected dosage of a substance according to the medical history metadata.

5. The method of claim 1, wherein the simulation comprises:
   detecting, based at least in part on the medical history metadata, an alarm condition; and
   indicating the alarm condition to a user.

6. The method of claim 1, comprising generating artificial medical image data based on the received medical image data, and based on the medical history metadata.

7. The method of claim 1, wherein the medical image data is received from one of: a computerized tomography (CT) system, a magnetic resonance imaging (MRI) system, a X-Ray system, a positron emission tomography (PET) system, an Ultrasound system, a picture archiving and communication systems (PACS) archive and a fluoroscopy system.

8. The method of claim 1, comprising storing the computerized simulation procedure as a procedure plan in at least one of: a patient's primary metadata and a DICOM header.

9. An article comprising a non-transitory computer-readable storage medium, having stored thereon instructions, that when executed on a computer, cause the computer to:
   receive medical image data related to a specific patient;
   receive medical history metadata related to health-care patient records of the specific patient not including the medical image data;
   generate a patient-specific digital image-based model of an anatomical structure of the specific patient that exhibits a simulated patient-specific physiological behavior, wherein the simulated patient-specific physiological behavior is based on the medical image data and the medical history metadata related to at least one of the health-care patient records of the specific patient and the patient-specific digital image-based model is to be used in a computerized simulation of the image-guided medical procedure, wherein the patient-specific digital image-based model comprises a three-dimensional (3D) anatomical model of an anatomical structure, and wherein the patient-specific digital image-based model is displayed on a display; and
   simulate an image-guided procedure using the patient-specific digital image based model, the simulation comprising applying a force feedback to a physical medical tool operated by a physician using the simulation, the simulated patient-specific physiological behavior including that the patient-specific digital image-based model's interaction with the physical medical tool is based in part on the medical history metadata.

10. The method of claim 1 wherein the patient-specific metadata comprises one or more of: information related to a medical history or condition of a patient, diseases, allergies, sensitivity to drugs, and age.

11. The method of claim 1 wherein any of the interaction, reaction or response comprise one or more of blood vessel elasticity, rate of blood flow, response to certain drugs or different drug dosage, bone strength, rupture probability, sensitivity to radiation, and vessel reaction to various balloon inflation pressures.

12. The article of claim 9, wherein the computerized simulation comprises manipulating the digital image-based model according to the medical history metadata.

13. The article of claim 9, wherein the instructions when executed further cause the computer to:
   suggest, based at least in part on the medical history metadata, at least one physical medical tool to be used in the image-guided procedure;
   receive a selection of a physical medical tool from a user; and
   provide a simulated model of the selected physical medical tool, wherein the simulation comprises manipulating the simulated model of the selected physical medical tool and wherein said simulated physiological behavior comprises an interaction with the simulated model of the physical medical tool according to the medical history metadata.

14. The article of claim 9, wherein the instructions when executed further result in:
   suggesting, based at least in part on the medical history metadata, a dosage of a substance to administer; and
   receiving a selection of a dosage of a substance, wherein said simulated physiological behavior comprises a reaction to the selected dosage of a substance according to the medical history metadata.

15. The article of claim 9, wherein the instructions when executed further result in:
   detecting, based at least in part on the medical history metadata, an alarm condition; and
   indicating the alarm condition to a user.

16. The article of claim 9, wherein the instructions when executed further configure the computer to generate artificial medical image data based on the received medical image data, and based on the medical history metadata.

17. The article of claim 9, wherein the medical image data is received from one of: a computerized tomography (CT) system, a magnetic resonance imaging (MRI) system, a X-Ray system, a positron emission tomography (PET) system, an Ultrasound system, a picture archiving and communication systems (PACS) archive and a fluoroscopy system.

18. The article of claim 9, wherein the instructions when executed further configure the computer to store the computerized simulation procedure as a procedure plan in at least one of: a patient's primary metadata and a DICOM header.

19. A non-transitory computer readable storage medium having instructions stored thereon that when executed by a computing device result in:
   receiving medical image data related to a specific patient;
   receiving, by the computing device, medical history metadata related to health-care patient records of the specific patient, the medical history metadata not including the medical image data; and
   generating, by the computing device, a patient-specific digital image-based model of an anatomical structure of the specific patient based on the medical image data and the medical history metadata and using the patient-specific digital image-based model in a simulation wherein the patient-specific digital image-based model exhibits a simulated patient-specific physiological behavior based on the medical history metadata, the simulation comprising applying a force feedback to a physical medical tool operated by a physician using the simulation, the simulated patient-specific physiological behavior including that the patient-specific digital image-based model's interaction with the physical medical tool is based in part on the medical history metadata.

20. The non-transitory computer readable storage medium of claim 19, wherein the instructions when executed further result in performing the computerized simulation of the image-guided procedure using the patient-specific digital image-based model.

* * * * *